United States Patent [19]

Williams

[11] Patent Number: 5,593,434
[45] Date of Patent: Jan. 14, 1997

[54] STENT CAPABLE OF ATTACHMENT WITHIN A BODY LUMEN

[75] Inventor: Michael S. Williams, Cupertino, Calif.

[73] Assignee: Advanced Cardiovascular Systems, Inc., Santa Clara, Calif.

[21] Appl. No.: 473,003

[22] Filed: Jun. 7, 1995

Related U.S. Application Data

[62] Division of Ser. No. 91,453, Jul. 14, 1993, Pat. No. 5,423,885, which is a continuation of Ser. No. 830,219, Jan. 31, 1992, abandoned.

[51] Int. Cl.⁶ ............................. A61F 2/06; A61M 29/00
[52] U.S. Cl. .................................. 623/1; 623/12; 606/195
[58] Field of Search ............................ 623/1, 11, 12; 604/8; 606/194, 195; 600/36

[56] References Cited

U.S. PATENT DOCUMENTS

| | | | |
|---|---|---|---|
| 4,470,207 | 4/1988 | Kreamer | 623/1 |
| 4,879,135 | 11/1989 | Greco et al. | 623/1 |
| 4,969,896 | 11/1990 | Shors . | |
| 5,007,926 | 4/1991 | Derbyshire | 623/1 |
| 5,059,211 | 10/1991 | Slack et al. | 606/198 |
| 5,078,726 | 1/1992 | Kreamer | 623/1 |
| 5,133,732 | 7/1992 | Wiktor | 606/195 |
| 5,135,536 | 8/1992 | Hillstead | 606/195 |
| 5,167,614 | 12/1992 | Tessmann | 604/8 |
| 5,423,851 | 6/1995 | Samuels | 623/1 |
| 5,423,885 | 6/1995 | Williams | 623/12 |

FOREIGN PATENT DOCUMENTS

| | | | |
|---|---|---|---|
| 0335341 | 4/1989 | European Pat. Off. . | |
| 0420541 | 3/1991 | European Pat. Off. . | |
| 0364787 | 4/1992 | European Pat. Off. . | |
| 2164562 | 3/1986 | United Kingdom | 623/1 |

*Primary Examiner*—Debra S. Brittingham
*Attorney, Agent, or Firm*—Fulwider Patton Lee & Utecht

[57] ABSTRACT

An expandable, balloon catheter delivered intravascular stent, especially adapted for cardiovascular applications, having a plurality of protrusions on its outer surface for engaging the artery walls in which it is disposed. The protrusions are formed from the body of the stent in a unitary, one-piece manner. Apertures are formed in the stent body from the space vacated in the body by the material forming the protrusions. When the stent is expanded by the balloon catheter, the protrusions engage both the apertures and the artery walls, to lock the stent into the expanded diameter. In this way axial displacement and radial collapse of the stent is avoided. The protrusions are arranged in a plurality of shapes, sizes and patterns. The stent may be made of a bioabsorbable material and/or a therapeutic drug delivery material.

17 Claims, 1 Drawing Sheet

STENT CAPABLE OF ATTACHMENT WITHIN A BODY LUMEN

This application is a divisional of application Ser. No. 08/091,453, filed Jul. 14, 1993, now U.S. Pat. No. 5,423,885, which is a continuation of application Ser. No. 07/830,219, filed Jan. 31, 1992, now abandoned.

BACKGROUND OF THE INVENTION

1. Field of the Invention

The present invention generally relates to expandable endoprosthesis devices, in particular expandable intraluminal vascular grafts, generally called stents, which are adapted to be implanted into a patient's lumen, such as a blood vessel, to maintain the patency of the vessel. These devices are frequently used in the treatment of atherosclerotic stenosis in blood vessels, especially after percutaneous transluminal coronary angioplasty (PTCA) procedures, to prevent restenosis of a blood vessel. The present invention also relates to an expandable intraluminal vascular graft that can be used in any body lumen, and be used for drug delivery.

2. Description of Related Art

In expandable stents that are delivered with expandable catheters, such as balloon catheters, the stents are positioned over the balloon portion of the catheter and expanded from a reduced diameter to an enlarged diameter greater than or equal to the artery wall, by inflating the balloon. Stents of this type can be expanded and held in an enlarged diameter by deformation of the stent (e.g., Palmaz U.S. Pat. No. 4,733,665), by engagement of the stent walls with respect to one another (e.g., Kreamer U.S. Pat. No. 4,740,207; Beck et al. U.S. Pat. No. 4,877,030; and Derbyshire U.S. Pat. No. 5,007,926), and by one-way engagement of the stent walls together with endothelial growth into the stent (e.g., Stack et al. U.S. Pat. No. 5,059,211).

SUMMARY OF THE INVENTION

The present invention is directed to providing a stent, adapted to be attached within a body vessel, designed to expand and remain in an enlarged diameter form by engaging, through protuberances on the stent, both the vessel walls that the stent is expanded against and the stent walls themselves. The stent has a plurality of projections on the stent walls that engage and interact with a plurality of apertures, thereby providing a locking mechanism as the stent is expanded. Further, some of the projections engage the vessel walls of a patient to secure the stent at a desired location in the vessel.

A further object of the present invention is to provide a stent having a plurality of different geometric projections on its walls, in any combination of sizes and shapes, for securing the stent in a vessel.

Another object of the present invention is to design a stent that is capable of localized therapeutic drug delivery.

Yet another object of the present invention is to design a stent that is bioabsorbable.

These and other advantages of the invention will become more apparent from the following detailed description thereof when taken in conjunction with the accompanying drawings.

DETAILED DESCRIPTION OF THE INVENTION

Figure 1:
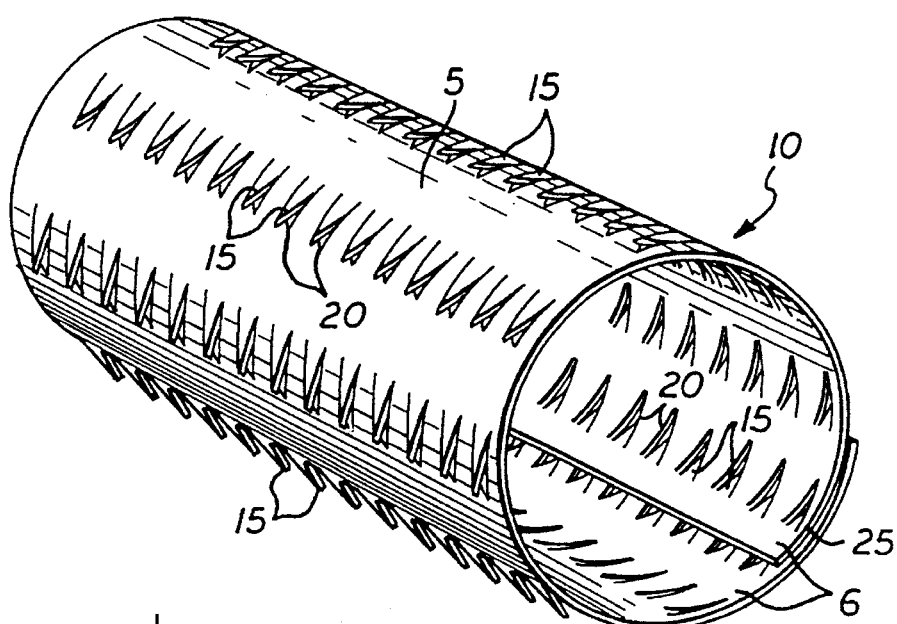
FIG. 1 shows a perspective view of one embodiment of the present invention, showing a stent in a non-expanded form.

As shown by the embodiment of FIG. 1, a stent 10 is formed, in its natural state prior to expansion, in a cylinder having protrusions or teeth 15 on one side of the stent, forming a roughened outer wall or exterior surface 5 that is adapted to lie contiguous with an arterial wall. Teeth 15 of roughened outer wall or exterior surface 5 of stent body 10 are designed to engage the arterial walls and endothelium layer of a blood vessel, and in general would engage the walls of a body lumen to help retain the stent in place.

Figure 2:
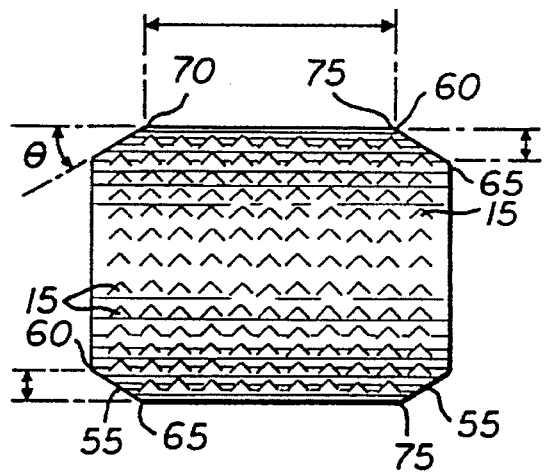
FIG. 2 shows an axial view of another embodiment of the present invention, employing shallower dimensioned protrusions.

The teeth 15 are cut away from a sheet of material which is then curled into a cylinder. The cylinder has a wall thickness 25 at its end. In the embodiment of FIG. 2 the wall thickness of the stent tapers towards the ends, to form a beveled end surface, as explained below, to give greater flexibility and vessel compliance to the stent, as explained below.

Apertures 20 correspond to the recesses of body 10 left behind when teeth 15 were cut away from the body. Apertures 20 thus have the same outline as teeth 15.

As can be seen in the FIG. 1 embodiment, teeth 15 are arranged in rows extending axially (longitudinally) along the stent body, and have a sharp, narrow "V" shape. Although in this embodiment a sharp "V" shape is employed, in general practically any shaped protrusion may be employed. The teeth create a roughened surface texture on the body.

Furthermore, while in all the embodiments shown the protrusions are found on one side of the body, namely the outer wall of the stent body, the side lying against the artery, it is possible to have protrusions or projections on either or both sides of the body.

In the embodiment of FIG. 1, teeth 15 project out from about the long length and circumference of the exterior surface or outer wall 5 of body 10, the side adjacent to the artery wall. The teeth can thus engage the stent wall in a positive manner. The interior surface or inner wall 6 of body 10 is the side facing the bloodstream, and is substantially free of any projections.

In the preferred embodiment shown in FIG. 1, the teeth are formed from body 10 in a one-piece or unitary manner, being cut from the same sheet of material that constitutes the body. The portion of the body thus removed becomes a tooth or protrusion, leaving an aperture 20 in the body having substantially the same shape as the tooth. Apertures 20 are thus defined by the portion of the body removed to form the teeth or protrusions. The teeth may be formed by injection-molding, casting, lasing, etching, plasma and corona techniques, or machining.

Also in the preferred embodiment of FIG. 1, body 10 is formed from a sheet of material curled into a cylinder, with the sheet having overlapping edges, as can be seen in FIG.

1. Also as is readily apparent from FIG. 1, the overlapping edges allow the exterior surface or outer wall 5 to contact the interior surface or inner wall 6 of the cylinder forming the stent. The protrusions 15 on the outer wall, which make the outer wall rougher than the inner wall, permit the outer wall to engage the apertures in the inner wall, and, together with the engagement of the protrusions with the blood vessel, hold the stent in place in an enlarged diameter form in the patient's vasculature.

While in the preferred embodiments disclosed herein protrusions 15 were formed from the body in the form of triangular teeth, in general the protrusions may be formed in any shape and in any manner, including adding the protrusions to a smooth body made of the same or different material from the protrusions, or treating the body to create a roughened surface texture, with or without apertures in the body.

Furthermore, while any material may be employed to form the stent of the present invention, preferably a Food and Drug Administration (FDA) approved material for use in this environment is employed, that is, a biocompatible material. Metals such as stainless steel, Ni—Ti, platinum (Pt), Nitinol™, tantalum (Ta) or gold (Au) may be used.

A plastic that is biocompatible may be used. The biocompatible plastic may also be bioabsorbable, that is, biodegradable. For instance, a polymer from the linear aliphatic polyester family, such as poly(lactic acid), poly(glycolic acid) or polycaprolactone, and their associated copolymers, may be employed. Degradable polymers such as polyorthoester, polyanhydride, polydioxanone and polyhydroxybutyrate may also be employed.

When the stent is expanded by an expanding device, such as a balloon catheter, teeth 15 engage apertures 20 to lock the stent open in an expanded diameter form. A plurality of teeth 15 hold the stent in an expanded diameter form by engaging apertures 20 and the arterial walls. By engaging the arterial walls, teeth 15 on roughened side 5 also prevent the stent from being axially displaced along the artery.

Expansion of stent 10 from a reduced diameter form into an expanded diameter form is preferably performed by a balloon catheter. Any other means for expanding the stent, however, may be used. Briefly, and in general terms, when the stent is to be deployed in a coronary artery the stent is placed over a balloon catheter that has been prepared for PTCA angioplasty. The catheter is percutaneously introduced into a vessel, following a previously positioned guidewire in an over-the-wire angioplasty catheter system, and tracked by a fluoroscope, until the balloon portion and associated stent are positioned at the point where the stent is to be placed. Thereafter the balloon is inflated and the stent is expanded by the balloon portion from a reduced diameter form to an expanded diameter form. After the stent has been expanded to its final expanded diameter, the balloon is deflated and the catheter is withdrawn, leaving the stent in place.

It should be understood that the present stent is not limited to use in coronary arteries and over-the-wire angioplasty catheter systems, but the stent may be deployed in any body lumen by any suitable mechanical means, which includes hydraulic expansion.

To facilitate the placement of the stent of the present invention, the stent may be impregnated with a radiopaque material, making it opaque, and therefore visible, to X-rays. Suitable radiopaque materials include iodine based materials and solutions thereof, and barium salts, including materials containing iodipamide (sold commercially under the trade name Cholografin), iopanoic acid (sold under the trade name Telepaque), barium sulfate, bismuth trioxide, bismuth oxychloride, or powdered metals, such as tantalum, gold, platinum and palladium.

It is further envisioned that the stent may be impregnated with a therapeutic agent to provide localized drug delivery.

When the stent has been expanded to its final form, the stent is affixed in place by a combination of the teeth in the body engaging apertures in the body of the stent, as well as the teeth engaging the walls of the artery, including the endothelium layer. It is believed that the endothelium layer of the artery will grow into the stent over a short period of time (in 7 to 21 days), to further help retain the stent in place. The stent may be made of a bioabsorbable material, such as the material as disclosed above, so that eventually the stent will dissolve. Endothelium layer growth into the stent and the modified surface texture of the stent ensures that pieces of the stent will not discharge into the bloodstream and cause an embolism as the stent is dissolved.

It can be seen that one of the features of the present invention includes maintaining an expandable stent in an enlarged diameter or operative form in a body lumen, by providing a roughened surface texture on the outside surface of the stent that engages both the lumen wall and the stent itself.

Figure 3:
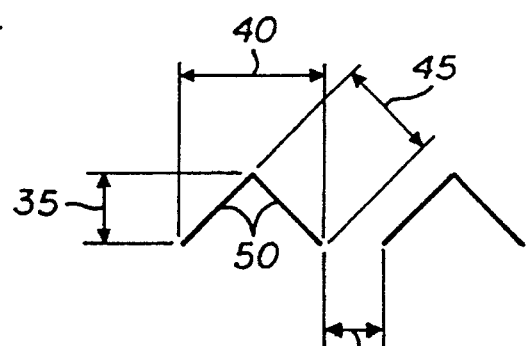
FIG. 3 shows the dimensions of the protrusions in FIG. 2.

Turning now to FIG. 2, a protrusion pattern for a second embodiment of the present invention is disclosed. The stent of the second embodiment substantially corresponds in structure to the embodiment disclosed in FIG. 1, with the principle difference being the geometric shape and spacing of the teeth, and the beveling of the ends, to be described below. In the FIG. 1 embodiment teeth 15 form a sharp, narrow "V" shape, whereas in the second embodiment teeth 35 are less pointed, and form a wider "V" shape. As shown in FIG. 3, height 35 of the apex of the "V" is 0.010 in, width 40 at the mouth of the "V" is 0.020 in., and the length of side 45 is 0.014 in. Sides 50 of each tooth are spaced at 90° to one another at the apex. The teeth are spaced along the circumference of the stent in rows, each row spaced 0.0189 in. from one another, as indicated in reference No. 57.

As can be seen in FIG. 2, another modification of the stent of the second embodiment is the presence of beveled ends 55. As can be seen from the drawings, beveled ends 55 are defined as those portions of the cylindrical stent that lie along the longitudinal (axial) axis of the cylinder, spaced from one another by approximately the longitudinal length of the stent. Beveled ends 55 allow the stent to be more compliant and flexible at its ends, so that the ends can more easily match the flexibility of the vessel walls that the stent is embedded in, and allow the stent to be more vessel compliant. Beveled ends 55 taper from a larger wall thickness away from the ends to a smaller wall thickness at the very end of the stent, as can be seen from the drawing. For instance, on the right hand side the stent is beveled along a portion of the stent starting from point 65, defining the right hand end of the stent, to 75. In a symmetrical fashion the left hand side of the stent end is beveled, with both beveled ends having an angulation θ. As is readily apparent the wall thickness of the stent along the beveled portion is less than the wall thickness of the stent outside the beveled portion.

The height of the bevel from points 60 and 65 is 0.055 in., while the length of the straight portion of the stent from points 70 and 75 is 0.455 in, with the overall length from end to end being 0.600 in.

Figure 4:
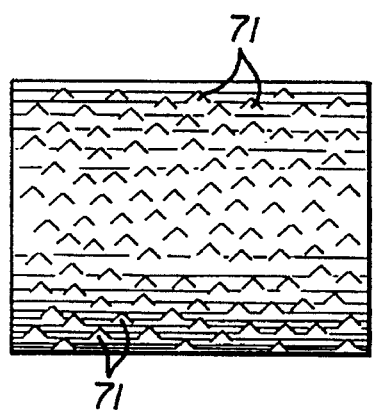
FIG. 4 shows an axial view of a third embodiment of the present invention, employing a random dispersion of protrusions.

Another embodiment of the present invention is shown in FIG. 4. In this embodiment, the tooth pattern is substantially random, with protrusions 70 scattered throughout the body of the stent, which is formed from a sheet curled into a cylinder, as in the other embodiments. The operation of this embodiment of stent is the same as the other embodiments, with the teeth engaging apertures in the body, as well as engaging the walls of the vessel the stent resides in, when the stent is expanded into an enlarged diameter form.

Again it should be understood that while in the above embodiments the protrusions on the body were formed from the body, in general the protrusions may be formed in any manner, including adding the protrusions to a smooth body made of the same or different material from the protrusions, or treating the body to create a roughened surface texture, with or without apertures in the body. As before, the surface texture forming the protrusions may be formed via plasma techniques, corona techniques, molding, casting, lasing, etching, machining, or any other technique that changes the surface texture of the body.

Furthermore, it should be understood that the dimensions set forth for the above embodiments are not intended to limit the invention to only those dimensions. For example, while certain dimensions might be appropriate for a stent used in a coronary artery, these same dimensions might not be suitable for a stent used in other parts of a patient's vasculature or body lumen.

Other modifications can be made to the present invention by those skilled in the art without departing from the scope thereof.

I claim:

1. A method of securing an intravascular stent in a patient's vasculature, comprising:

placing an intravascular stent over a balloon catheter, said stent having a length and circumference, a plurality of protrusions projecting from about the length and circumference of said stent, and a plurality of apertures about the length and circumference of said stent;

positioning said intravascular stent in a patient's vasculature with said balloon catheter;

expanding said balloon catheter to expand said stent from a reduced diameter to an enlarged diameter form; and securing said stent in said patient's vasculature when said stent is in said enlarged diameter form, said securement occurring through said protrusions engaging said apertures as well as said protrusions engaging said patient's vasculature.

2. The method of claim 1, wherein the step of positioning the intravascular stent in the patient's vasculature includes the further step of:

percutaneously introducing the stent and balloon catheter into the patient's vasculature.

3. The method of claim 2, wherein the step of percutaneously introducing the catheter into the patient's vasculature includes the step of:

following the catheter along a previously positioned guidewire in the patient's vasculature.

4. The method of claim 2, including the further steps of:

deflating the balloon catheter; and withdrawing the balloon catheter from the patient's vasculature, whereby the intravascular stent remains secured in the patient's vasculature.

5. The method of claim 1, including the further step of:

impregnating the intravascular stent with a therapeutic agent to provide localized drug delivery to the patient's vasculature.

6. A method of securing a stent within a body lumen, comprising:

placing a stent over an expandable catheter, said stent having a length and circumference, a plurality of protrusions about said length and circumference, and a plurality of apertures about said length and circumference;

introducing the stent and expandable catheter into a body lumen;

positioning said stent at a desired location in the body lumen with said expandable catheter;

expanding said expandable catheter to expand said stent from a reduced diameter to an enlarged diameter form; and securing said stent in said enlarged diameter form at the desired location in said body lumen, said securement occurring through said protrusions securing said stent in its enlarged diameter form, said protrusions engaging against walls of said body lumen.

7. The method of claim 6, including the further steps of:

deflating the expandable catheter; and withdrawing the catheter from the body lumen, whereby the stent is left in the desired location in the body lumen.

8. The method of claim 6, including the further step of:

impregnating the stent with a therapeutic agent to provide localized drug delivery to the body lumen.

9. The method of claim 6, including the further step of:

impregnating the stent with a radiopaque material.

10. The method of claim 6, wherein the step of positioning the stent at the desired location includes the further step of:

tracking the location of the stent with a fluoroscope.

11. A method of securing a stent within a body lumen, comprising:

placing a stent over an expandable catheter, said stent having a length and circumference, a plurality of protrusions projecting along said length and circumference, and a plurality of apertures about said length and circumference, said apertures corresponding to the shape of the protrusions;

introducing the stent and expandable catheter into a body lumen;

positioning said stent at a desired location in the body lumen with said expandable catheter;

expanding said expandable catheter to expand said stent from a reduced diameter to an enlarged diameter form;

locking said stent in said .enlarged diameter form, said locking occurring through one or more of the protrusions engaging one or more of the apertures; and securing said stent at the desired location in said body lumen, said securement occurring through said protrusions engaging against walls of said body lumen.

12. The method of claim 11, including the further steps of:

cutting the protrusions from a generally planar sheet of biocompatible material, the protrusions unitary with and secured to the planar sheet; and curling the sheet into a cylinder to form said stent.

13. The method of claim 12, wherein the step of cutting the protrusions includes forming apertures in the sheet, said apertures formed in said sheet as a result of the protrusions being cut from the sheet.

14. The method of claim 13, wherein the step of cutting the protrusions includes cutting the protrusions in a substantially "V" shape.

15. The method of claim 12, wherein the step of cutting the protrusions includes dispersing the protrusions on the sheet in a random pattern.

16. The method of claim 12, wherein the step of cutting the protrusions includes spacing the protrusions from one another in a substantially uniform manner to form rows of protrusions.

17. The method of claim 12, wherein the sheet has at least two ends, the method including the further step of:

beveling one or more ends of the sheet.

* * * * *